United States Patent [19]

Kupleian

[11] 4,227,913

[45] Oct. 14, 1980

[54] INHIBITING PLANT BUD GROWTH WITH SUBSTITUTED 2,6-DINITROANILINES

[75] Inventor: Robert H. Kupleian, Bucks County, Pa.

[73] Assignee: American Cyanamid Company, Stamford, Conn.

[21] Appl. No.: 934,442

[22] Filed: Aug. 17, 1978

Related U.S. Application Data

[60] Division of Ser. No. 439,193, Feb. 4, 1974, Pat. No. 4,123,250, which is a continuation-in-part of Ser. No. 245,646, Apr. 19, 1972, abandoned, which is a continuation-in-part of Ser. No. 158,538, Jun. 30, 1971, abandoned.

[51] Int. Cl.$^3$ .................. A01N 43/36; A01N 33/06; A01N 41/00
[52] U.S. Cl. ......................................... 71/78; 71/76; 71/95; 71/103
[58] Field of Search .................. 71/78, 76, 121, 95

[56] References Cited

U.S. PATENT DOCUMENTS

| | | | |
|---|---|---|---|
| 3,257,190 | 6/1966 | Soper | 71/94 |
| 3,321,292 | 5/1967 | Soloway et al. | 71/103 |
| 3,518,076 | 6/1970 | Wright | 71/103 |
| 3,672,864 | 6/1972 | Maravetz | 71/121 |
| 3,672,866 | 6/1972 | Damiano | 71/121 |
| 3,764,624 | 10/1973 | Strong et al. | 71/121 |
| 4,066,441 | 1/1978 | Lutz et al. | 71/121 |
| 4,077,795 | 3/1978 | Cooke et al. | 71/78 |
| 4,123,250 | 10/1978 | Kupelian | 71/78 |

FOREIGN PATENT DOCUMENTS

| | | | |
|---|---|---|---|
| 45-8999 | 1/1970 | Japan | 71/103 |
| 212181 | 5/1968 | U.S.S.R. | 71/103 |

Primary Examiner—Glennon H. Hollrah
Attorney, Agent, or Firm—H. G. Jackson

[57] ABSTRACT

Novel compositions and a method for inhibiting bud growth on plants comprising contacting said plants with a bud growth inhibiting amount of certain substituted 2,6-dinitroanilines are disclosed.

6 Claims, No Drawings

INHIBITING PLANT BUD GROWTH WITH SUBSTITUTED 2,6-DINITROANILINES

This is a division of application Ser. No. 439,193 filed Feb. 4, 1974 which is now U.S. Pat. No. 4,123,250 (10-31-1978) which is a continuation-in-part of abandoned Ser. No. 245,646 filed Apr. 19, 1972 which is a continuation-in-part of abandoned Ser. No. 158,538 filed June 30, 1971.

This invention relates to a method and compositions for inhibiting bud growth on plants. More particularly, this invention relates to the application of bud-growth inhibiting amounts of certain substituted 2,6-dinitroanilines to plants.

In the practice of the horticultural sciences, a means for inhibiting the growth of plant buds is commonly desired. Growth of suckers from axial buds on commercial crops reduces fruit yields and, in the case of tobacco, adversely affects the development of marketable leaves. Uncontrolled development of terminal buds also adversely affects plants and crop yield. Furthermore, uncontrolled adventitious and terminal bud development on harvested tubers and bulbs such as in potatoes and onions, is also advantageously avoided.

A conventional method to insure an adequate supply of nutrients to crop leaves and fruits is to physically remove the undesired bud growth. Plant height is controlled by removing the stem apex. In the case of tobacco, this involves removal of flowers and some top leaves near the stage of plant maturity. This process is commonly known as "topping". In the case of axillary buds, or suckers, the undesired sucker growth is generally removed by hand, in a laborious and time consuming process.

Accordingly, it is an object of this invention to provide a convenient chemical method for inhibiting bud growth on plants without adversely affecting the crop leaves and fruits or other desirable and useful parts thereof. Another object is to provide chemical compositions effective in controlling bud growth. A further object is to provide compositions which will not introduce toxic residues in crop leaves and fruits when applied in bud inhibiting amounts to plants. Other objects and advantages will be apparent from the description of the invention which follows.

It has been found that certain substituted 2,6-dinitroanilines are effective for controlling bud growth on plants. These compounds have the following formula:

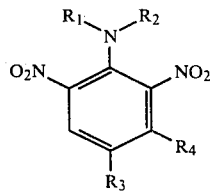

wherein $R_1$ is hydrogen; $R_2$ is isopropyl, 1,3-dimethylbutyl, secondary $C_4$–$C_6$ alkyl groups free from quaternary carbon atoms and free from branching at the penultimate carbon atom, 1-(methoxymethyl)propyl or 2-methoxy-1-methylethyl; $R_1$ and $R_2$ taken together with the nitrogen are

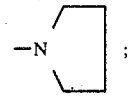

$R_3$ is methyl, chloro, methylsulfonyl or trifluoromethyl; and $R_4$ is methyl or methoxy.

The following compounds are illustrative of preferred compounds which are useful in the process of this invention: N-sec-butyl-2,6-dinitro-3-methyl-4-(methylsulfonyl)aniline; 3,4-dimethyl-2,6-dinitro-N-(3-pentyl)aniline; N-sec-butyl-3,4-dimethyl-2,6-dinitroaniline; 4-chloro-2,6-dinitro-N-[1-methoxymethyl)propyl]-m-toluidine; 3,4-dimethyl-2,6-dinitro-N-(2-methoxy-1-methylethyl)aniline; 3-methoxy-2,6-dinitro-N-(3-pentyl)-p-toluidine; 4-chloro-2,6-dinitro-N-(1,3-dimethylbutyl)-m-toluidine; 1-(2,6-dinitro-3,4-xylyl)-pyrrolidine; 3,4-dimethyl-2,6-dinitro-N-(2-pentyl)aniline; 3,4-dimethyl-2,6-dinitro-N-(3-hexyl)aniline; N-sec-butyl-3-methyl-4-chloro-2,6-dinitroaniline; 4-chloro-2,6-dinitro-N-(3-pentyl)-m-toluidine; 4-chloro-2,6-dinitro-N-(2-pentyl)-m-toluidine; 4-methylsulfonyl-2,6-dinitro-N-(3-pentyl)-m-toluidine and 4-trifluoromethyl-2,6-dinitro-N-(3-pentyl)-m-toluidine.

Suitable methods for preparing certain of the active ingredients are well known in the literature. See, for example, U.S. Pat. No. 3,257,190. Others are exemplified below.

In the practice of the method of the present invention, the aniline compounds are applied to the plants in which bud control is desired. The active ingredients generally possess systemic activity and, accordingly, while direct contact between the active ingredient and the bud may be desired, it is generally not required. Accordingly, application can be made to the foliage of the plants, or in the case of harvested bulbs and tubers application can be made directly thereto. The active ingredients are preferably employed in combination with conventional horticultural adjuvants and formulation aids. They may be used in combination with solid or liquid adjuvants, and formulated as dusts, dust concentrates, wettable powders, and liquids. Field application can be made by conventional techniques, such as, with powder dusters, boom and hand sprayers, spray dusters and the like.

The active ingredient may initially be formulated as a concentrated composition, comprising the active ingredient in a solid or liquid adjuvant which serves as a formulation aid or conditioning agent, permitting the concentrates to be further mixed with a suitable solid or liquid carrier, in a form which enables prompt assimilation by the plant systems.

Useful liquid adjuvants in which the toxicant is dissolved, suspended to distributed include, for example, the following organic solvents and mixtures thereof: hexane, benzene, toluene, acetone, cyclohexanone, methyl ethyl ketone, isopropanol, butanediol, methanol, xylene, dioxane, isopropyl ether, methylene dichloride, tetrachloroethylene, hydrogenated naphthalene, solvent naphtha, and petroleum fractions, such as, kerosene.

Useful solid adjuvants in which the toxicant may be absorbed or dispersed on or in include, for example: natural clays, such as china clays, bentonites, attapulgites; other natural materials, such as, talc, pyrophyllite, quartz, diatomaceous earth, fuller's earth, chalk, rock phosphate, kaolin, kieselguhr volcanic ash, and sulfur; chemically modified materials, such as, acid washed bentonite, precipitated calcium phosphate, precipitated calcium carbonate, calcined magnesia, and colloidal silica; and other materials such as powdered cork, powdered wood and powdered pecan walnut shells. For maximum absorption and ease of handling, these materials are used in finely divided form of particles which range in size from 20 to 40 mesh (tyler) or finer. Prior to field application, the solid and liquid concentrate compositions are generally diluted by the addition of a solid or liquid carrier. Suitable solid carriers, in which the concentrate compositions are mixed or absorbed on or in, include: the previously mentioned solid adjuvants; fertilizers, such as, ammonium nitrate, urea, superphosphate, composite, manure and humus; pesticides; other herbicides; sand and the like. Suitable liquid carriers in which the concentrate compositions are dissolved, suspended or emulsified or dispersed include, for example, water and the liquid adjuvants previously mentioned.

Dust formulations can be prepared by grinding about 0.01% to about 25% by weight of the active compound with about 99.99% to about 75% by weight of a solid inert diluent.

Dust concentrates are made in a similar fashion excepting that the percentage by weight of the active ingredient is increased to from about 25% to about 75% by weight of the composition.

Wettable powder formulations useful in the practice of this invention can be prepared by grinding together from about 25% to 75% by weight of the active compound with about 15% to 65% of a finely divided solid carrier, such as attaclay, kaolin, diatomaceous earth or talc; about 2% to 5% by weight of a dispersant, such as sodium lignosulfonate; and from about 2% to 5% by weight of an anionic-nonionic emulsifier, such as those set forth in Table I below. Such wettable powder formulations are dispersed in water or other nonphytotoxic liquids for application.

Aqueous solutions and/or suspensions are preferred formulations. Concentrations of the active ingredient in the range of from about 100 ppm to about 4,000 ppm are generally effective in the control of axial bud growth. Compositions of lower concentration are generally suitable for the control of sprouting on tubers and bulbs. For example, compositions having the active ingredient present in concentrations of from about 10 ppm to about 1,000 ppm are generally effective in the control of sprouting on white potatoes and onions. This can be achieved by simply dipping them for a period of from about 30 seconds to 90 seconds in a solution of the active ingredient and permitting them to dry.

Typical liquid formulations are set forth in Table I below. In each case, the percentages indicated are by weight.

TABLE I

Liquid Formulation A
  45%—N-sec-butyl-3,4-dimethyl-2,6-dinitroaniline
  5%—nonylphenoxy polyoxyethylene ethanol
  50%—xylene
Liquid Formulation B
  35%—3,4-dimethyl-2,6-dinitro-N-(3-pentyl)aniline.
  5%—anionic-nonionic emulsifier calcim myristylbenzenesulfonic acid and the oleate ester of a polyoxyethylene glycol (molecular weight=350)
  60%—xylene
Liquid Formulation C
  40%—4-chloro-2,6-dinitro-N-(1,3-dimethylbutyl)-m-toluidine
  7%—anionic-nonionic emulsifier from B (above)
  53%—xylene Typical wettable powder formulations which may be used in the practice of the present invention are set forth in Table II below.

TABLE II

Wettable Powder Formulation A
  40%—3,4-dimethyl-2,6-dinitro-N-(3-pentyl)aniline
  50%—attaclay
  5%—sodium lignosulfonate
  5%—nonylphenoxy polyoxyethylene ethanol
Wettable Powder Formulation B
  35%—N-sec-butyl-3,4-dimethyl-2,6-dinitroaniline
  60%—diatomaceous earth
  3%—sodium lignosulfonate
  2%—anionic-nonionic emulsifier calcium myristylbenzenesulfonic acid and the oleate ester of polyoxyethylene glycol (molecular weight=350)
Wettable Powder Formulation C
  50%—N-sec-butyl-2,6-dinitro-3-methyl-4-(methylsulfonyl)aniline
  45%—kaolin
  3%—dispersant (Marasperse ® N, a neutral sodium lignin sulfonate by Marathon Corp.)
  2%—anionic-nonionic blend emulsifier
Wettable Powder Formulation D
  40%—4-chloro-2,6-dinitro-N-[1-(methoxymethyl)-propyl]-m-toluidine
  54%—attaclay
  3%—dispersant (Marasperse ® N)
  3%—sodium dioctyl sulfosuccinate In tobacco farming, bud growth is conventionally controlled by two mechanical processing operations. As previously stated, plant height is regulated by cutting off the terminal bud flower of the tobacco plant in a process known as "topping". This process facilitates the development of the large leaf which forms the commercial crop. Their development is, however, offset by the enhanced development of lateral (axillary) buds. The lateral growth (called "sucker growth") again reduces the nutrient supply available for large leaf development. This necessitates a second mechanical operation namely, the hand removal of the suckers from each tobacco plant. In the practice of the present invention, the inconvenient and expensive mechanical steps can be avoided by two spraying operations. Firstly, terminal bud development can be controlled by an overspraying of the active ingredient. Secondly, sucker development can be controlled by a subsequent spraying of the plant step and foliage.

Harvesting of the marketable or prime leaves of flue-cured tobacco is usually begun about one to two weeks after treatment and may continue for four or five weeks. Usually the leaves are cut from the bottom of the stalk in groups of three at weekly intervals. Inhibiting growth of axillary buds during this period is important since such treatment results in improved quality, texture, and yield of the prime or marketable leaves. Inhibiting growth of axillary buds on topped burley tobacco is also important from the standpoint of improving quality and yield of tobacco, although the harvesting procedure is somewhat different. Accordingly, after the burley tobacco is topped, it is sprayed with a solution of the active material to inhibit axillary bud development, and the whole stalk is then harvested in accordance with standard practices some 5 to 10 weeks after treatment.

Examples illustrating preparation of active ingredients and objects and advantages of the present invention are further demonstrated by the examples set forth below. They are not, however, to be taken as being limitative thereof. In each case, parts and percentages set forth herein are by weight unless otherwise indicated.

EXAMPLES 1-16

Control of Axillary Tobacco Buds

Seedling tobacco plants are transplanted into six-inch plastic pots containing a greenhouse soil mix (loam soil:sand:muck, 1:1:1). The plants are grown in the greenhouse for eight to ten weeks and then topped just above the eleventh node. The active ingredients are applied as foliar sprays to the entire plant, immediately after topping. Each spray solution is prepared by dissolving the desired amount of active ingredient in an acetone-water mixture containing 0.5% Tween 20, polyoxyethylene sorbitan monolaurate (Atlas Powder Co.). The plant to be sprayed is placed on a turntable and 65 ml. of the spray solution applied to the plant from three directed hozzles. The concentration of active ingredient in the spray solution varies from 100 ppm to 1600 ppm. After spraying, the plants are placed at random on a greenhouse bench and watered normally for a period of two weeks. At the termination of each test, the suckers are removed from all nodes, weighed and the results expressed as percent inhibition compared with the fresh weight of suckers from untreated controls. The results achieved are set forth in Table III below. Maleic hydrazide, a commercial bud growth regulant (Example 1) and N-sec-butyl-4-t-butyl-2,6-dinitroaniline (Example 15) of U.S. Pat. No. 3,672,866 (1972) are included for comparison.

TABLE III

| Ex. No. | Structure | Percent Inhibition | | | | |
|---|---|---|---|---|---|---|
| | | 1600 ppm. | 800 ppm. | 400 ppm. | 200 ppm. | 100 ppm. |
| 1 | maleic hydrazide | 99 | 98 | 89 | 80 | 51 |
| 2 | 2,6-dinitro-3,4-dimethyl-N-(sec-butyl)aniline | 97 | 97 | 97 | 94 | 86 |
| 3 | 2,6-dinitro-3,4-dimethyl-N-(isopropyl)aniline | 99 | 99 | 93 | 91 | 51 |
| 4 | 2,6-dinitro-3,4-dimethyl-N-(3-pentyl)aniline | 97 | 96 | 99 | 93 | 95 |
| 5 | 2,6-dinitro-3,4-dimethyl-N-(2-pentyl)aniline | 97 | 97 | 95 | 96 | 28 |

TABLE III-continued

| Ex. No. | Structure | Percent Inhibition | | | | |
|---|---|---|---|---|---|---|
| | | 1600 ppm. | 800 ppm. | 400 ppm. | 200 ppm. | 100 ppm. |
| 6 | NH-CH(CH₃)(C₂H₅), 2,6-dinitro-4-chloro-3-methylphenyl | 98 | 99 | 98 | 97 | 91 |
| 7 | NH-CH(CH₃)(CH₂CH₃), 2,6-dinitro-3-methyl-4-(SO₂CH₃)phenyl | 94 | 98 | 97 | 97 | 77 |
| 8 | NH-CH(CH₃)₂, 2,6-dinitro-3-methyl-4-(SO₂CH₃)phenyl | 12 | 12 | 15 | 3 | 30 |
| 9 | N-pyrrolidinyl-2,6-dinitro-3,4-dimethylphenyl | 97 | 84 | 84 | 57 | 26 |
| 10 | NH-CH(C₂H₅)(CH₂CH₃), 2,6-dinitro-4-chloro-3-methylphenyl | 96 | 96 | 96 | 95 | 94 |
| 11 | NH-CH(CH₃)(CH₂CH₂CH₃), 2,6-dinitro-4-chloro-3-methylphenyl | 93 | 97 | 96 | 91 | 87 |
| 12 | NHCH(C₂H₅)(C₂N₅), 2,6-dinitro-3-methyl-4-(SO₂CH₃)phenyl | 98 | 76 | 75 | 98 | 98 |
| 13 | NH-CH(C₂H₅)(C₂H₅), 2,6-dinitro-4-chloro-3-methylphenyl | 98 | 95 | 80 | 96 | 92 |

TABLE III-continued

| Ex. No. | Structure | Percent Inhibition | | | | |
|---|---|---|---|---|---|---|
| | | 1600 ppm. | 800 ppm. | 400 ppm. | 200 ppm. | 100 ppm. |
| 14 | 4-CF$_3$-2,6-dinitro-N-(1-ethylpropyl)-3-methylaniline | 98 | 96 | 95 | 98 | 95 |
| 15 | 4-(tert-butyl)-2,6-dinitro-N-(sec-butyl)aniline | 95 | 98 | 97 | 89 | 35 |
| 16 | N-(1-ethylbutyl)-3,4-dimethyl-2,6-dinitroaniline | NT | NT | NT | 98 | NT |

EXAMPLE 17

Preparation of N-(Ethoxycarbonyl)-3,4-dimethylaniline

The above-named compound is prepared by first dissolving 51.5 grams of 3,4-dimethylaniline in 250 ml. of benzene. Then, while maintaining the solution at a temperature in the range of between 20° C. and 30° C., a benzene solution containing 23.9 grams of ethyl chloroformate is slowly added. The mixture is permitted to stand overnight at room temperature and then filtered. The filtrate is stripped by evaporation under vacuum, leaving the desired product, in the form of a dark purple liquid weighing 30 grams.

EXAMPLE 18

Preparation of N-(Ethoxycarbonyl)-3,4-dimethyl-2,6-dinitroaniline

Concentrated sulfuric acid (30 ml.) is added to a cold solution of concentrated nitric acid (84 ml.). The resulting solution is then chilled to form −5° C. to −10° C. and 30 grams of N-(ethoxycarbonyl)-3,4-dimethylaniline slowly added to the nitrating mixture with external cooling. The mixture is then poured onto ice and extracted with ethyl ether. The extract is then washed with water and with aqueous sodium bicarbonate solution. The ether is then removed by evaporation leaving an oil which is crystallized from absolute ethanol to produce 3 grams of the desired product in the form of a yellow solid, having a melting point of 51° C.–54° C.

EXAMPLE 19

Preparation of 3,4-Dimethyl-2,6-Dinitroaniline

Into 30 ml. of concentrated sulfuric acid is added 2.85 grams of N-(ethoxycarbonyl)-3,4-dimethyl-2,6-dinitroaniline. The mixture is heated to a temperature in the range of from 110° C. to 120° C. for 15 minutes and then poured over ice. The precipitated solid is collected and crystallized from absolute ethanol yielding the desired product having a melting point of from 141.5° C. to 142.5° C.

EXAMPLE 20

Preparation of 1-Chloro-3,4-dimethyl-2,6-dinitrobenzene

A cuprous chloride solution is prepared by dissolving 3.24 g. of CuSO$_4$.5H$_2$O in water and adding NaCl to the warm solution. While holding the blue solution in an ice bath, a solution of 1.24 grams of sodium meta-bisulfite and 0.52 gram NaOH in 12 ml. of water is added. A white precipitate forms which is dissolved in 12 ml. of concentrated hydrochloric acid.

Two grams of 3,4dimethyl-2,6-dinitroaniline is dissolved in 40 ml. of warm glacial acetic acid. The solution is cooled to room temperature and a mixture of 0.9 grams of sodium nitrite in 7 ml. of cold concentrated sulfuric acid is added very slowly, producing a solid in the mixture. This mixture is then added to the solution of cuprous chloride in concentrated hydrochloric acid to form a diazonium mixture.

The diazonium mixture is then warmed producing the desired product as a solid precipitate. The solid is isolated by filtration and purified by recrystallization from cyclohexane. The desired product has a melting point of 109° C. to 111° C.

The procedure is repeated using 16 grams of the 3,4-dimethyl-2,6-dinitroaniline, yielding 11.0 grams of the desired product, having a melting point of 111° C. to 113° C.

EXAMPLE 21

Preparation of
N-Isopropyl-3,4-dimethyl-2,6-dinitroaniline

4-Chloro-3,5-dinitro-o-xylene (10.0 grams, 0.043 mole) and isopropylamine (10.1 grams, 0.17 mole) are mixed and refluxed for 12 hours using an efficient reflux condenser. The mixture is then cooled and poured into 100 ml. of 5% hydrochloric acid and extracted with diethyl ether. The ether extract is dried over magnesium sulfate. Removal of the drying agent and solvent leaves an orange oil which readily solidifies. The product is recrystallized from methanol to give 8.7 grams (80%) of an orange solid with melting point 69° C. to 70° C.

EXAMPLE 22

Preparation of
N-sec-Butyl-3,4-dimethyl-2,6-dinitroaniline

A mixture of 4-chloro-3,5-dinitro-o-xylene (140 grams, 0.61 mole), sec-butylamine (184 ml, 1.82 moles), and xylene (1400 ml) is brought to reflux. After refluxing overnight, the reaction mixture is cooled and filtered. The precipitate is washed with petroleum ether. The filtrate and washings are combined, washed with 500 ml. of 10% hydrochloric acid, and finally with 2 liters of water. The organic layer is separated and dried. Removal of the drying agent and the solvent leaves an orange oil which crystallizes with the addition of petroleum ether. A yellow orange solid (150.6 grams, 86.5%) with melting point 42° C. to 43° C. is collected.

EXAMPLES 23 to 25

Following the general procedures of Examples 21 and 22, substituting the appropriate amine for the amines used therein, yields products having the following formula and properties set forth in Table IV below.

TABLE IV

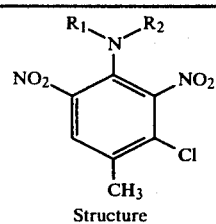

| Ex. No. | Structure R₁ | R₂ | m.p. °C. | Crystallizing Solvent |
|---|---|---|---|---|
| 23 | H | —CH(C₂H₅)₂ | 56–57 | methanol |
| 24 | H | —CHCH₂CH₂CH₃<br>\|<br>CH₃ | 42–43 | methanol |
| 25 | (pyrrolidinyl) | | 120–122 | cyclohexane |

EXAMPLES 26–27

Preparation of
N-sec-butyl-3-chloro-4-methyl-2,6-dinitroaniline

A mixture of 10.04 g. (0.04 mole) of 2,4-dichloro-3,5-dinitrotoluene, 5.85 g. (0.08 mole) of sec-butylamine and 200 ml. of cyclohexane is stirred at reflux for six hours. The mixture is filtered and the filtrate is evaporated at reduced pressure. The filtrate is partitioned between ether and dilute hydrochloric acid. The organic phase is washed with water and brine, dried over magnesium sulfate and evaporated in vacuo. Crystallization of the residue from ethanol gives 7.71 g. of orange crystals, m.p. 40°–46° C. Two recrystallizations from ethanol give the analytical sample, m.p. 45°–47° C. Analysis Calcd. for $C_{11}H_{14}ClN_3O_4$: C, 45.92; H, 4.90; Cl, 12.32; N, 14.61. Found: C, 45.96; H, 4.97; Cl, 12.36; N, 14.78.

Following the above procedure and substituting the appropriate amine for sec-butylamine yields products of the following structure having melting points set forth in Table V below.

TABLE V

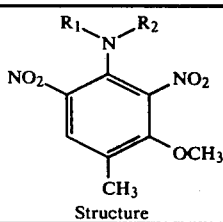

| Ex. No. | R₁ | R₂ | m.p. °C. |
|---|---|---|---|
| 26 | —H | —CHCH₂CH₃<br>\|<br>CH₃ | 45–47 |
| 27 | —H | —CH(CH₃)₂ | 67–70 |

EXAMPLE 28

Preparation of
N-isopropyl-4-methyl-3-methoxy-2,6-dinitroaniline

To a stirred solution of 5.47 g. (0.02 mole) of 3-chloro-N-isopropyl-4-methyl-2,6-dinitroaniline in 100 ml. of methanol is added 1.79 g. (0.033 mole) of sodium methoxide. The reaction mixture is stirred at reflux for three hours, cooled to room temperature and filtered. The filtrate is evaporated at reduced pressure and the residue partitioned between ether and dilute aqueous hydrochloric acid. The organic phase is successively washed with water, saturated sodium bicarbonate and brine. It is then dried over anhydrous magnesium sulfate. Evaporation of the solvent in vacuo gives 5.0 g. of the desired product having a m.p. of 72°–77° C. Two recrystallizations from methanol give the analytical sample, m.p. 77.5°–79° C. Analysis: Calcd. for $C_{11}H_{15}N_3O_5$: C, 49.07; H, 5.62; N, 15.61. Found: C, 49.35; H, 5.66; N, 15.77.

Following this general procedure using the appropriate sodium alkoxide and chloroaniline, compounds having the following formula were prepared. The melting points observed are set forth in Table VI below.

TABLE VI

| Ex. No. | R₁ | R₂ | m.p. °C. |
|---|---|---|---|
| 29 | H | —CHCH₂CH₃<br>\|<br>CH₃ | oil |

TABLE VI-continued

Structure:
R1,R2-N attached to benzene ring with NO2 at 2,6-positions, OCH3 at 3-position, CH3 at 4-position

| Ex. No. | R₁ | R₂ | m.p. °C. |
|---|---|---|---|
| 30 | H | —CH(C₂H₃)₂ | 47–51 |

EXAMPLE 31

Preparation of 4-chloro-N-isopropyl-3-methyl-2,6-dinitroaniline

To a stirred mixture of 10.04 g. (0.04 mole) of 3,6-dichloro-2,4-dinitrotoluene in 50 ml. of ethanol is added 9.0 g. (0.15 mole) of isopropylamine. The mixture is stirred at room temperature for two hours and then at reflux for one hour. The solution is allowed to cool to room temperature and the crystalline precipitate is filtered and washed with a small amount of hexane to give 10.2 g. of the desired product as golden crystals having a m.p. of 69°–73° C. Two recrystallizations from methanol give the analytical sample, m.p. 69°–70° C. Analysis: Calcd. for C₁₀H₁₂ClN₃O₄: C, 43.88; H, 4.42; Cl, 12.96; N, 15.35. Found: C, 44.09; H, 4.43; Cl, 13.02; N, 15.42.

The reactions of the other primary amines with 3,6-dichloro-2,4-dinitrotoluene are carried out in analogous fashion. In cases where the product crystallizes with difficulty the solvent is evaporated and the product isolated by extraction Following the general procedure above, substituting the appropriate amine yields compounds of the following structure. The melting points observed are set forth below in Table VII.

TABLE VII

Structure: R1,R2-N attached to benzene ring with O2N at 2-position, NO2 at 6-position, CH3 at 3-position, Cl at 4-position

| Ex. No. | R₁ | R₂ | m.p. °C. |
|---|---|---|---|
| 33 | H | —CHCH₂CH₃ with CH₃ branch | oil |
| 34 | H | —CH(CH₂CH₃)₂ | 41.5–44.0 |
| 35 | H | —CHCH₂CH₂CH₃ with CH₃ branch | 31–32 |

EXAMPLES 36–38

Preparation of N-sec-butyl-3-methyl-2,6-dinitro-4-(trifluoromethyl)aniline

A nitration mixture, consisting of 16.1 ml. of H₂SO₄ (d 1.84) and 1.9 ml. of HNO₃ (d 1.5) is heated to 55° C. and 3.5 g. of 5-chloro-2-(trifluoromethyl)toluene is slowly added. The mixture is heated for 1 hour at 55° C. followed by 1 hour at 110° C. The reaction mixture is cooled and poured onto ice to give 5-chloro-2-(trifluoromethyl)-4,6-dinitrotoluene as a cream colored solid precipitate which is crystallized from cyclohexane to give 3.6 g. of cream colored crystals having a m.p. of 81°–82° C.

5-Chloro-2-(trifluoromethyl)-4,6-dinitrotoluene (1.8 g.) is refluxed with 15 minutes with 3 ml. of sec-butylamine and 30 ml. of benzene. The reaction mixture is cooled and the desired product as a solid precipitate is removed by filtration, washed with water until neutral, dried and vacuum stripped to give 1.5 g. of N-sec-butyl-3-methyl-2,6-dinitro-4-(trifluoromethyl)aniline as a yellow solid, m.p. 38°–39° C.

Compounds having the following structure and melting points are forth in Table VIII were prepared by the above general procedure substituting the appropriate amine for the sec-butylamine usd therein.

TABLE VIII

Structure: R attached to benzene ring with NO2 at 2,6-positions, CH3 at 3-position, CF3 at 4-position

| Ex. No. | R | m.p. °C. |
|---|---|---|
| 37 | —NH—CH(CH₃)₂ | Yellow crystals, 75°–76° |
| 38 | —NHCH(C₂H₅)₂ | 44°–45° |

EXAMPLE 39

Preparation of 3-Chloro-6-(methylsulfonyl)-2,4-dinitrotoluene

To a slurry of 4-(methylsulfonyl)-2,6-dinitro-m-cresol (4.9 g.) in phosphorus oxychloride (21 ml.), N,N-dimethylaniline is added at such a rate that the temperature does not exceed 34° C. When the addition is complete and the initial exotherm has subsided, the mixture is heated to 60°–65° C. and held there for 10 minutes. The reaction mixture is carefully decomposed by pouring into a ice and water mixture. The desired product as a precipitated solid (4.49 g.) is collected and recrystallized from benzene-pet ether to give a solid with m.p. of 174°–175° C. Analysis: Calcd. for C₈H₇ClN₂O₆S: C, 32.59; H, 2.37; N, 9.50; S, 10.86; Cl, 12.05. Found: C, 32.62; H, 2.37; N, 9.39; S, 10.65; Cl, 12.25.

EXAMPLES 40–44

Preparation of N-(1-methylbutyl)-4-(methylsulfonyl)-2,6-dinitro-m-toluidine

A mixture of 3-chloro-6-(methylsulfonyl)-2,4-dinitrotoluene (10.0 g., 0.034 mole) and 2-aminopentane (6.1 g. 0.07 mole) is refluxed in benzene (75 ml.) for 4 hours. After standing overnight, the mixture is successively washed with dilute hydrochloric acid, water, a 5% aqueous potassium carbonate solution and finally water. The mixture is then dried over magnesium sulfate. Removal of the magnesium sulfate and solvent leaves the desired product as a yellow oil which readily crystallized on cooling. The crude product is recrystallized from ethanol to give 9.5 grams with m.p. 85°–88° C.

Using the above general procedure, substituting the appropriate amine for the 2-aminopentane used therein, compounds of the following structure are prepared. Their melting points are set forth in Table IX below.

TABLE IX $$\text{O}_2\text{N}-\underset{\underset{\text{SO}_2\text{CH}_3}{\underset{|}{\text{C}_6\text{H}_2(\text{CH}_3)}}}{\text{C}_6\text{H}_2}-\text{N}(R_1)(R_2)\text{, NO}_2$$

| Ex. No. | R₁ | R₂ | m.p. °C. |
|---|---|---|---|
| 41 | H | —CH(CH₃)—C₃H₇-n | 85°–88° |
| 42 | H | iso-C₃H₇ | 156°–158° |
| 43 | H | sec-C₄H₉ | 66.5°–69° |
| 44 | H | —CH(C₂H₅)—C₂H₅ | 135°–136° |

EXAMPLES 45–49

Following the procedure set forth in Example 29 but utilizing the appropriate sodium alkoxide and chloroaniline, yields the compound of Example 45.

Following the procedure of Example 21, and using the appropriate 1-chloro-3,4-(disubstituted)-2,6-dinitrobenzene and appropriate amine, yields the compounds of Examples 46 and 49. Similarly, the procedure of Examples 32 and 40, with substitution of appropriate reactants yield the compounds of Examples 47 and 48 respectively.

TABLE X

| Ex. No. | R₁ | R₂ | R₃ | R₄ | m.p. °C. |
|---|---|---|---|---|---|
| 45 | H | —CH(C₂H₅)₂ | —Cl | —OCH₃ | 51–54 |
| 46 | H | —CH(CH₃)—CH₂OCH₃ | —CH₃ | —CH₃ | oil |
| 47 | H | —CH(CH₂OCH₃)—C₂H₅ | —Cl | —CH₃ | 36–38 |
| 48 | H | —CH(CH₃)—CH₂OCH₃ | —SO₂CH₃ | —CH₃ | 126–128 |
| 49 | H | —CH(C₂H₅)—CH₂OCH₃ | —CH₃ | —CH₃ | 46–47.5 |

EXAMPLE 50

The procedure of Examples 1 through 16 above is repeated utilizing 4-chloro-N-(1-ethylpropyl)-2,6-dinitro-m-toluidine and 4-chloro-N-(1-ethylpropyl)-2,6-dinitro-m-anisidine as test compounds and maleic hydrazide as a standard. Two weeks after treatment, the suckers are removed from all nodes of the treated tobacco plants, weighed and the results expressed as percent inhibition compared with the fresh weight of suckers from untreated controls. The results achieved are set forth in the table below. Maleic hydrazide, a commercial bud growth regulant, is included for comparison.

In similar tests, the compounds of Examples 45 through 49 applied on tobacco plants at the 1600 ppm. rate, provide from 50% to 99% inhibition of suckers.

TABLE XI

| Structure | Percent Inhibition | | | | |
|---|---|---|---|---|---|
| | 1600 ppm. | 800 ppm. | 400 ppm. | 200 ppm. | 100 ppm. |
| O₂N—C₆H₂(Cl)(OCH₃)—NH—CH(C₂H₅)₂, NO₂ | 98 | 96.9 | 96.5 | 98.4 | 97.6 |
| O₂N—C₆H₂(Cl)(CH₃)—NH—CH(C₂H₅)₂, NO₂ | 98 | 98 | 98 | 98.6 | 98.4 |
| Maleic Hydrazide | 99.8 | 98.4 | 98 | 78.9 | 78.3 |

EXAMPLE 51

The following tests were conducted to determine the bud growth inhibiting effect of the compounds of the present invention on woody plants such as fruit and nut trees. Where said compounds are applied in bud growth inhibiting amounts with a horticultural adjuvant to fruit trees, for example, prior to the budding thereon, adventitious branching is effectively inhibited thereon as illustrated below.

Red Delicious apple trees, approximately 8 years old, were sprayed prior to budding with aqueous solutions containing test compound. A Trombone hand pump sprayer with an adjustable hollow cone nozzle designed to produce moderately coarse droplet size was used. One-half gallon of aqueous solution containing 1200 ppm. of test compound was applied to each tree. Untreated controls were used for comparison. Applications were made in early spring, and trees were examined periodically throughout the growing season for interior adventitious branching. Final examinations were made in late summer and early fall about 3 to 4 months after treatment. Results obtained are reported below.

TABLE XII

| Compound Structure | Rate ppm | Adventitious Budding On Trunks and Interior Branching |
|---|---|---|
| O₂N—C₆H₂(CH₃)(CH₃)—HN—CH(CH₃)—C₂H₅, NO₂ | 1200 | None |
| Control | 0 | Heavy sprouting Trunk and Branches |

The data in Table XIII illustrates the tobacco bud growth inhibition properties of compounds of the invention at 200 ppm compared to analogous compounds.

Application of the compounds to the plants is the same as that of Examples 1-16, above.

The data in Table XIV further illustrate control of axillary tobacco buds. Application of the compounds to

TABLE XVIII

TOBACCO BUD GROWTH INHIBITION TESTS

| COMPOUND OF INVENTION | | COMPARATIVE COMPOUND | CONCENTRATION IN PPM | % BUD INHIBITION |
|---|---|---|---|---|
| 4-Cl-2,6-dinitro-3-methyl-N-(1-methoxymethylpropyl)aniline | vs | 3,5-dinitro-4-methyl-N-(1-methoxymethylpropyl)aniline | 200 vs 200 | 99.1% vs 63.4% |
| 2,6-dinitro-3,4-dimethyl-N-(sec-butyl)aniline | vs | 2,6-dinitro-4-methyl-N-(sec-butyl)aniline | 200 vs 200 | 94% vs −6% |
| 2,6-dinitro-3,4-dimethyl-N-(3-pentyl)aniline | vs | 2,6-dinitro-4-methyl-N-(3-pentyl)aniline | 200 vs 200 | 99.5% vs 13.4% |
| 2,6-dinitro-3-methoxy-4-methyl-N-(3-pentyl)aniline | vs | 2,6-dinitro-4-methyl-N-(3-pentyl)aniline | 200 vs 200 | 97.6% vs 13.4% |
| 2,6-dinitro-3,4-dimethyl-N-(1-methoxymethylethyl)aniline | vs | 2,6-dinitro-3-methyl-N-(3-methoxypropyl)aniline | 200 vs 200 | 84.3% vs 53% | the plants is the same as that of Examples 1-16, above. EXAMPLE 64 is an art compound.

TABLE XIV

TOBACCO BUD GROWTH INHIBITION TESTS

| | | Percent Inhibition | | | |
|---|---|---|---|---|---|
| | | 1000 ppm | | 200 ppm | |
| Ex. No. | Structure | Fresh Wt. g. suckers | % Control | Fresh Wt. g. suckers | % Control |
| 52 | 4-Cl-2,6-dinitro-3-methyl-N-(1-methoxymethylpropyl)aniline | 1.1 | 94.8 | 0.2 | 99.1 |

TABLE XIV-continued
TOBACCO BUD GROWTH INHIBITION TESTS

| # | Structure | A | B | C | D |
|---|-----------|---|---|---|---|
| 53 | 1-(NH-CH-C$_3$H$_7$n), 2-NO$_2$, 3-CH$_3$, 4-CH$_3$, 6-NO$_2$ benzene | 0.1 | 99.6 | 1.0 | 95.2 |
| Acetone/Water Control | | 22.6 | — | 21.0 | — |
| 54 | 1-(NH-CH(CH$_3$)-C$_2$H$_5$), 2-NO$_2$, 3-CH$_3$, 4-CH$_3$, 6-NO$_2$ benzene | 0.3 | 99.7 | 0.9 | 99.0 |
| 55 | 1-(NH-CH(CH$_3$)-C$_2$H$_5$), 2-NO$_2$, 3-CH$_3$, 4-SO$_2$CH$_3$, 6-NO$_2$ benzene | 0.3 | 99.7 | 0.9 | 99.0 |
| 56 | 1-(NH-CH(C$_2$H$_5$)-C$_3$H$_7$n), 2-NO$_2$, 3-CH$_3$, 4-CH$_3$, 6-NO$_2$ benzene | 0.4 | 99.6 | 0.9 | 99.0 |
| Acetone/Water | | Average 10 repeats 9.3 | — | — | — |
| 57 | 1-(NH-CH(CH$_3$)-CH$_2$CH(CH$_3$)$_2$), 2-NO$_2$, 3-CH$_3$, 4-Cl, 6-NO$_2$ benzene | 0.1 | 99.5 | 0.1 | 99.5 |
| 58 | 1-(NH-CH(C$_2$H$_5$)-C$_2$H$_5$), 2-NO$_2$, 3-CH$_3$, 4-CH$_3$, 6-NO$_2$ benzene | 0.1 | 99.5 | 0.1 | 99.5 |
| 59 | 1-pyrrolidinyl, 2-NO$_2$, 3-CH$_3$, 4-CH$_3$, 6-NO$_2$ benzene | 1.1 | 94.8 | 0.7 | 96.7 |

TABLE XIV-continued
TOBACCO BUD GROWTH INHIBITION TESTS

| Ex. No. | Structure | | | | |
|---|---|---|---|---|---|
| 60 | 2,6-dinitro-3-methoxy-4-methyl-N-(3-pentyl)aniline | 0.1 | 99.5 | 0.5 | 97.6 |
| 61 | 2,6-dinitro-N-(1-methoxy-2-propyl)-3,4-dimethylaniline | 1.1 | 94.8 | 3.3 | 84.3 |
| 62 | 2,6-dinitro-3-methoxy-N-(2-butyl)-4-(trifluoromethyl)aniline | 4.4 | 79.1 | 17.0 | 19.1 |
| Acetone/Water Controls | | 11.2 | — | — | — |
| 63 | 2,6-dinitro-N-(2-pentyl)-3,4-dimethylaniline | 0.3 | 99.5 | 1.03 | 81.2 |
| Acetone/Water Control | | 4.8 | — | — | — |
| | | 6.2 | — | — | — |
| 64 | 4-tert-butyl-2,6-dinitro-N-(2-butyl)aniline | .12 | 99.16 | .29 | 98.9 |

| | | Percent Inhibition | | | | |
|---|---|---|---|---|---|---|
| Ex. No. | Structure | 1600 ppm | 800 ppm | 400 ppm | 200 ppm | 100 ppm |
| 65 | 2,6-dinitro-3-methoxy-4-methyl-N-(2-butyl)aniline | 96.1 | 83.8 | 87.8 | 82.4 | 61.4 |

I claim:

1. A method for inhibiting bud growth on plants comprising contacting the plants with a bud growth inhibiting amount of the compound [N-sec-butyl-2,6-dinitro-3-methyl-4-(methylsulfonyl)aniline] N-sec-butyl-4-methylsulfonyl-2,6-dinitro-m-toluidine, 1-(2,6-dinitro-3,4-dimethylphenyl)pyrrolidine or 4-methylsulfonyl-2,6-dinitro-N-(3-pentyl)-m-toluidine.

2. A method according to claim 1 for inhibiting the growth of axillary buds on tobacco plants comprising applying to the plants a bud growth inhibiting amount of the compound.

3. A method according to claim 1 for inhibiting the growth of axillary buds on tobacco plants comprising applying to the plants a bud growth inhibiting amount of the compound.

4. A method according to claim 3 wherein the compound is N-sec-butyl-4-methylsulfonyl-2,6-dinitro-m-toluidine.

5. A composition comprising a plant bud growth inhibiting amount of N-sec-butyl-4-methyl-sulfonyl-2,6-dinitro-m-toluidine, 1-(2,6-dinitro-3,4-dimethylphenyl)-pyrrolidine or 4-methylsulfonyl-2,6-dinitro-N-(3-pentyl)-m-toluidine and an inert carrier.

6. A composition according to claim 5 wherein the compound is N-sec-butyl-4-methylsulfonyl-2,6-dinitro-m-toluidine.

* * * * *